US008579188B2

(12) United States Patent
Cleary et al.

(10) Patent No.: US 8,579,188 B2
(45) Date of Patent: *Nov. 12, 2013

(54) METHODS OF IN-FIELD ANALYSIS

(75) Inventors: Michael Cleary, Liverpool (GB); Marcello Vitale, Flintshire (GB)

(73) Assignee: Smartwater Research Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/610,334

(22) Filed: Sep. 11, 2012

(65) Prior Publication Data

US 2013/0001300 A1  Jan. 3, 2013

Related U.S. Application Data

(63) Continuation of application No. 12/867,824, filed as application No. PCT/GB2009/000225 on Jan. 26, 2009, now Pat. No. 8,267,311.

(30) Foreign Application Priority Data

Jan. 26, 2008   (GB) .................................. 0801479.7

(51) Int. Cl.
*G06F 17/00* (2006.01)
(52) U.S. Cl.
USPC ...................... 235/375; 235/462.06
(58) Field of Classification Search
USPC .................. 235/375, 454, 462.06, 462.11
See application file for complete search history.

(56) References Cited

U.S. PATENT DOCUMENTS

| 3,989,938 | A | * | 11/1976 | Auth ................................ 702/24 |
| 5,319,437 | A | | 6/1994 | Van Aken et al. |
| 6,402,037 | B1 | * | 6/2002 | Prasad et al. .................... 235/487 |
| 7,315,667 | B2 | * | 1/2008 | Schmidt et al. .................. 385/12 |
| 8,267,311 | B2 | * | 9/2012 | Cleary et al. .................... 235/375 |
| 2002/0122878 | A1 | | 9/2002 | Kerns et al. |
| 2006/0181707 | A1 | | 8/2006 | Gibson et al. |
| 2006/0219961 | A1 | | 10/2006 | Ross et al. |
| 2007/0172429 | A1 | | 7/2007 | Gao et al. |

FOREIGN PATENT DOCUMENTS

| WO | 0250790 A1 | 6/2002 |
| WO | 2006050367 A2 | 5/2006 |
| WO | 2006053685 A2 | 5/2006 |

* cited by examiner

*Primary Examiner* — Daniel St. Cyr
(74) *Attorney, Agent, or Firm* — Pierce Atwood LLP; Joseph M. Maraia

(57) ABSTRACT

The present invention relates to the use of unique markers in the identification and tracking of objects. The present invention provides large numbers of unique markings for application to items as part of a marking system. The present invention provides a new approach to laboratory analysis and a means of rapid in-field identification of goods using a handheld scanner. It provides data that can be used as a means of product tracking, identification of counterfeit product and to prove ownership of stolen goods.

20 Claims, 1 Drawing Sheet

METHODS OF IN-FIELD ANALYSIS

RELATED APPLICATION(S)

This application is a continuation of U.S. application Ser. No. 12/867,824, filed Aug. 16, 2010, which is the U.S. National Stage of International Application No. PCT/GB2009/000225, filed on Jan. 26, 2009, published in English, which claims priority under 35 U.S.C. §119 or 365 to Great Britain Application No. 0801479.7, filed on Jan. 26, 2008. The entire teachings of the above applications are incorporated herein by reference.

BRIEF DESCRIPTION OF THE DRAWINGS

The foregoing will be apparent from the following more particular description of example embodiments of the disclosure, as illustrated in the accompanying drawings in which like reference characters refer to the same parts throughout the different views. The drawings are not necessarily to scale, emphasis instead being placed upon illustrating embodiments of the present disclosure.

A specific non-limiting embodiment of the invention will be described by way of example and with reference to the accompanying drawings in which.

DETAILED DESCRIPTION

Figure 1:
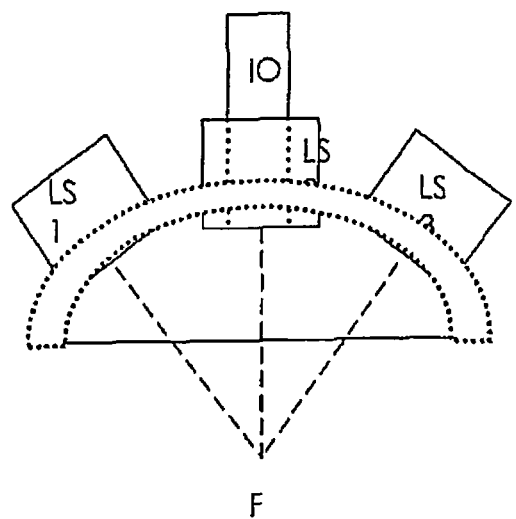
FIG. 1 illustrates a side section of the illumination head used to focus on the item being analysed in accordance with the present invention.

The present invention relates to the use of unique markers in the identification and tracking of objects. The present invention provides large numbers of unique markings for application to items as part of a marking system. The present invention provides a new approach to laboratory analysis and a means of rapid in-field identification of goods using a hand-held scanner. It provides data that can be used as a means of product tracking, identification of counterfeit product and to prove ownership of stolen goods.

The cost of counterfeit goods to the world community is immense. The present invention will help in the fight against counterfeit goods, which is a global market. Estimates vary, but this is generally accepted as being 6% of world trade or equivalent to £260 bn.

The main tracking mechanism in use currently is radio frequency identification (RFID). However, RFID does suffer from limitations. It cannot be covert, as although the chip is small, the antenna is generally big enough to be visible. It can be easily cloned by counterfeiters. RFID also suffers from being absorbed by water and reflected by metal surfaces. RFID tracking systems are also plagued by privacy/personal safety issues. Chip costs are also high.

Several systems are employed, or have been proposed in the patent literature, which apply some optical determination method for anti-counterfeit or tracking purposes. Most widespread are the simple UV- or IR-excited pigments formulated into inks and applied to banknotes, passports, ID or other high-value documents. Such inks are designed to be visually assessed, are immediately apparent to any would-be counterfeiter, easily replicated or even just imitated, since several substances would provide the same or very similar colours. Another one of their main weaknesses is the very limited number of visually distinguishable inks that can be produced, leading to the same luminescent features being used in the same documents over long periods, leaving ample time to counterfeiters for perfecting their copies.

Other systems aim to exploit spectroscopic analysis of some applied marker. For example, US2002001080 and references therein describe the use of absorption or reflectance spectroscopy, mainly applied to imaging of biological samples rather than security applications. WO2004114204 and US20050017079 describe the use of a combination of luminescent quantum dots. WO2006086998 describes a system where the relative intensity ratios in two luminescence bands are compared to one or more reference samples for validation, a system easily open to security breach if a counterfeiter were to be able to measure the reference samples.

All of these systems still suffer from the same basic problem as the simple visually-assessed luminescent inks, namely the limited number of combinations that are actually available to be used. Indeed, since all of the above systems rely on a limited set of data, from one or at most two types of spectra, the number of individual markers that can be discriminated in such systems is in the tens, hundreds or at most thousands, and relies mostly on a limited number of compounds that can be, therefore, identified and replicated by a skilled counterfeiter.

Another class of systems, exemplified by GB2319337 and by markers containing natural or synthetic DNA, require large-size, laboratory based instrumentation to be analysed and specific procedures to collect and preserve the samples before any analytical result is available. Although the number of individual markers available can be, in such cases, very large, indeed approaching the infinite, the lack of possible in-field analysis is a serious obstacle for many applications.

The approach presented herein overcomes the limitations of all the types of systems discussed.

The present invention relates to the use of unique markers in the identification and tracking of objects. It provides large numbers of unique markings for application to items as part of a marking system. It provides a new approach to laboratory analysis and a means of rapid in-field identification of goods using a hand-held scanner. It provides data that can be used as a means of product tracking, identification of counterfeit product and to prove ownership of stolen goods.

According to the present invention there is provided a method of sequentially collecting a plurality of spectral responses for analysing mixtures of materials, as claimed in claim 1 of the appended claims.

Also according to the present invention there is provided a method of verifying the authenticity of an item, as claimed in claim 7 of the appended claims.

Further according to the present invention there is provided an apparatus for analysing mixtures of materials used as a unique identifier, the mixtures of materials being applied to at least one object, as claimed in claim 12 of the appended claims.

Likewise according to the present invention there is provided a hand-held apparatus for remotely analysing mixtures of materials used as a unique identifier, the mixtures of materials being firstly applied to at least one item, as claimed in claim 21 of the appended claims.

It will be obvious to those skilled in the art that variations of the present invention are possible and it is intended that the present invention may be used, other than as specifically described herein.

The present invention provides a system for discriminating between counterfeit and genuine goods. It also provides a system for the tracking of manufactured goods both internally and after dispatch. The system can also be used by law enforcement agencies as it provides a covert marking system that can be used to identify the ownership of stolen goods, the premises from where they were stolen and any personnel present at the time of the offence.

The system is based on the tagging of items, directly as part of the item, on the surface of the item, on a label on the item, as part, on the surface or on a label on the primary (e.g., blister packs) or secondary (e.g. box) packaging. Preferred options are those in which the item itself is tagged. The most preferred option is the use of the tag as part of the item itself.

A wide range of tagging materials may be used including organics, inorganics, polymeric, molecular dyes or pigment, especially doped pigments, for example pigments doped with rare earth elements, q-dots or other nanomaterials, including materials micro- or nano-encapsulated or coated; delivered as paint or ink, in a film, incorporated in the bulk of the base material, for example as additives in polymeric and plastic materials, including polyolefin, polyesters and polycellulose, as a lubricant or a wetting agent or otherwise present on the surface and in the molecular-level surface roughness of the base material; tied to the base material by chemical bonds or by physical attraction forces.

The skilled person will appreciate that the virtually infinite level of coding is a major feature of the invention. The complexity is produced through the combined sequential use of multiple spectral dimensions in rapid succession, with multiple analyses being undertaken in seconds.

Sequential analysis using different stimuli, such as short wave UV, long wave UV, visible and IR, coupled with time-based differentiation through the study of phosphorescent decay rates or time-resolved spectra provides a multidimensional basis for the positive identification of known possible components in a mixture. This multi-dimensional spectral analysis provides a quantity of data unachievable with any individual technique.

The skilled person will appreciate that the following different stimuli could be used:

emission energy in the short and long UV, visible and near IR ranges, as a function also of stimulation energy absorption/reflectance of incident radiation over the same ranges energy relationship between stimulation and signal as in Raman spectroscopy relationship between stimulation and emission versus time as in phosphorescence spectroscopy The same approach may be taken through sequential analysis by instruments dedicated to each technique, although the time taken to do so and the ensuing costs argue strongly against this approach.

The present invention describes a scanner containing multiple different sources within the one body, allowing different forms of spectral analysis to be undertaken sequentially, being part of an overall system for generating mixtures; which provides a means of determining which of a series of preset components are present in said mixtures; which provides data management and optional telemetry systems; which allows rapid, possibly worldwide handling of data; and which provides information relevant to a wide range of applications.

When used as a method of identification applied to goods, the complexity of mixtures which can be produced approaches the infinite.

As an example of this approach, materials absorbing in the UV/visible and IR regions of the spectrum can be physically mixed with and used alongside materials emitting in various regions of the spectrum and those with other varying spectral properties. If one were using a silicon detector covering 400 nm to 950 nm, then the spectral range available limits the number of materials which may be used to form a coding sequence One embodiment would involve a detection element contained behind a series of narrow bandwidth filters. The filters are set to maximise transmission at the same wavelength as the maximum absorption/emission from the absorber/emitter.

Alternatively, the filter may be moved across the detector and the absorption/emission measured at each band-pass region to determine those components present. This may involve the use of a filter on a wheel which is spun in front of the detector and its position controlled and logged via simple software.

A further embodiment would comprise the use of a miniature spectrometer able to resolve incident radiation and provide information on intensity versus wavelength.

A further embodiment would involve a lens system to focus photons onto the detector cell of such a miniature spectrometer using free space optics or through a length of optical fibre. This would provide a way of maximising the signal from a small, inaccessible, or uneven surface not suitable for larger surface area detectors.

A further embodiment would provide a mechanism for simple unprocessed data to be transmitted from the hand-held scanner to a central server for processing, with the result then being transmitted back to the scanner.

For example, when used in absorption mode the scanner would select the correct source from those available to irradiate the area under analysis. Analysis of the reflected light would reveal the presence of additives through absorption of radiation at specific wavelengths. This analysis would be conducted over the visible and near infra-red (NIR) regions of the spectrum.

A further embodiment would allow Raman spectroscopy to be carried out through the use of an appropriate illumination source and detection range.

The device can also be used to measure different forms of spectral emission resulting from different forms of stimulation. Infra red, long and short wave light sources can be selected as required to provide information on the presence or absence of anti-stokes materials, materials emitting in response to long wave UV, materials emitting in response to short wave UV and so on. The device can also pulse these sources at preset time intervals so that phosphorescent materials with different decay rates can also be used as part of the coding process.

Light sources can be LED's or other light-emitting devices such as lasers, arc lamps, OLED's, incandescent sources etc.

All measurements are conducted sequentially and not simultaneously. This allows repeated analysis of the surface, using different spectral ranges in both absorption and emission. Data from each scan is stored and processed separately. The data from the different spectral measurements of each individual scan can be processed separately for simple cases; however, they are, in general, processed together in order to fully exploit the information therein contained.

The sequential processing of the multiple spectra produced by the invention may be used with various forms of spectral analysis including, but not limited to:

i) Visible absorption
ii) IR absorption
iii) Anti-stokes emissions
iv) Emissions with long wave UV stimulation
v) Emissions with short wave UV stimulation
vi) Emissions from phosphorescent materials under long wave UV with slow phosphorescent decay rate vii) Emissions from phosphorescent materials under long wave UV with medium phosphorescent decay rate viii) Emissions from phosphorescent materials under long wave UV fast phosphorescent decay rate ix) Emissions from phosphorescent materials under short wave UV with slow phosphorescent decay rate x) Emissions from phosphorescent materials under short wave UV with medium phosphorescent decay rate xi) Emissions from phosphorescent materials under short wave UV with fast phosphorescent decay rate xii) Raman spectroscopy As an example, the above set of techniques would result in twelve different data sets. Each data set will contain information indicating the presence or absence of various materials.

The in-field scanner can be made to different designs. One embodiment would involve:

Illumination head
Spectrometer
Telemetry unit
Firmware
Power supply
Visual Display Unit Whilst the skilled person can appreciate that many of the above aspects of the system are known in isolation, the accumulation and use of sequential analyses over different spectral and time domains as described is particularly advantageous. When used in-field the separate data sets may be collected and stored in separate buffers for subsequent analysis at the central server. Once all the data sets have been collected, they may then be transmitted to the central server, for example via an encrypted mobile phone/Internet link. A typical complete scan would take seconds to complete.

Figure 2:
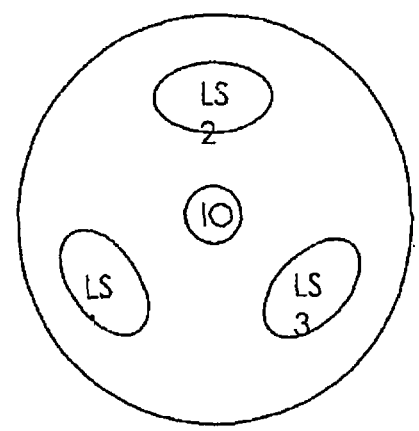
FIG. 2 shows a plan view from below of the illumination head shown in FIG. 1.

The combined sequential use of multiple spectral dimensions in rapid succession, with multiple analyses being undertaken in seconds is achieved through the illumination head and its connection to the spectrometer. When used to produce spectral emission the device has been designed to allow multiple excitation sources to focus on the area being analysed. An illumination head similar to that shown in FIGS. 1 and 2 could be used. As depicted, the head is based upon the three light sources (LS) above being focused onto the area being analysed (F). As discussed previously, they could for example, be a long wave UV LED, a short wave LED and an IR laser. Clearly both the UV LED's could be used for fluorescent and phosphorescent measurements. Assuming 3 different time delays for the phosphorescent measurements, this configuration alone could provide 9 different spectral ranges.

In the case of absorption/Raman analysis, interaction with the incident radiation takes place and the light then reflected, elastically or in-elastically, from the surface is directed through the input optics (IO) to the end of the optical fibre connected to the spectrometer.

The signal from the illumination head then enters the spectrometer. Various configurations can be used in order to maximise the sensitivity and/or resolution of the device, including transmittance optics, reflective optics, holographic gratings or a combination of them. Detectors can be bi-dimensional CCD's, one-dimensional diode arrays or single-point photomultipliers. In one embodiment, multiple detectors sensitive in different spectral regions might be used. In a further embodiment, different light-dispersing elements might be employed for different types of spectra.

With regard to the generation of mixtures, several options are available, that chosen depends upon which is best suited to the actual application. Assuming a qualitative argument initially, this can be based on the premise that a component is either present or not, i.e. options/component. On this basis, the number of codes available is 2 raised to the power given by the product of:

a) the number of components that can be discriminated in one data set and no other (even if their signal is present in several data sets), and b) the number of data sets collected For example 5 components separately detectable in each of 6 data sets will give a total number of codes equal to 230 or 109.

In a further embodiment, quantitative arguments may be used to further expand the codes available. In order to obtain the complexity required in this case, the concentration of each of the components could for example be increased stepwise by a power of 2. The concentration of each of 4 components of a 5 component mixture, with the 5th being an internal standard, would increase in steps, i.e. 1, 2, 4, 8. These primary concentration steps would then allow secondary concentrations to be used to fill in the gaps in the concentration range. The secondary concentration steps serve as identifiers in terms of the combination of primary concentrations that have been used to produce the secondary level, as shown below:

Primary 1 2 4 8

The final concentrations are used as identifiers to determine which ones of the primary concentration steps are present, e.g.

| Peak Height Relative to Internal Standard | Components Present |
| --- | --- |
| 0 | 0 |
| 1 | 1 |
| 2 | 2 |
| 3 | 1 + 2 |
| 4 | 4 |
| 5 | 1 + 4 |
| 6 | 2 + 4 |
| 7 | 1 + 2 + 4 |
| 8 | 8 |
| 9 | 1 + 8 |
| 10 | 2 + 8 |
| 11 | 1 + 2 + 8 |
| 12 | 4 + 8 |
| 13 | 1 + 4 + 8 |
| 14 | 2 + 4 + 8 |
| 15 | 1 + 2 + 4 + 8 |

Giving total concentration ranges for each component of: 0, 1, 2, 3, 4, 5, 6, 7, 8, 9, 10, 11, 12, 13, 14, 15, i.e., 16 concentration steps. Each primary concentration of a component is, effectively, a component in itself. Therefore, using 4 components, each possessing 4 primary concentration levels, affords 216 codes, or 65536 codes available using just one data set. If using, as in the qualitative example, 6 data sets, the number of codes available, overall, would be 2(16×6)=296, i.e. almost 8×1028. This embodiment allows a quantitative approach to be used to extend a qualitative argument by using secondary concentrations to indicate the presence or absence of each of the primary levels.

In a further embodiment, a wider spectral range could be covered by using a combination of detectors, for example, a silicon and an InGaAs. The device firmware would switch between detectors and combine the output from each to give a continuous spectrum covering a typical range for this combination of 400 to 1700 nm. A wider available spectral range would further increase the number of materials that could be discriminated in each separate data set, increasing yet again, as a consequence, the number of codes available.

This embodiment would increase the number of codes again, by an amount that is dependent upon the number of materials. If one assumes 13 components used in this range, with just 2 primary concentrations, i.e. 4 concentration steps, and 6 types of measurement, the total number of codes would be almost 1047.

In a further embodiment, the system may be used with a hand-held battery-powered scanner capable of remote in-field operation. All the necessary data handling can be provided by software residing on the scanner itself or on a separate local computer wired to the scanner or connected to it by short-range wireless communication methods. In this embodiment the system may be used typically to monitor and manage stock movement from point of manufacture or to validate tickets used in access control.

A further, preferred embodiment would involve the scanner contacting a central server from the field position as part of the field operation, via a suitable medium e.g. GPS, GPRS or satellite and transferring data back to the central server where the computations would be performed. The result of this analysis is then transmitted back to the field operative, who will then respond in a prescribed manner.

The results from the server may also be forwarded to the customer. This will allow the customer to update their own records in those areas important to them. The scanner location at the time of the measurement will also be transmitted to the central server. This will allow customers to check the final location of goods, in terms of country, region, customer location, all of which helps the customer to identify any potential diversion of their goods to unauthorised locations.

The response to the field operator may be as text, as symbols, as sound or vibration; the message can be of any level of detail, from a simple "yes/no" to a batch number or a description of the item, for a positive response, and instructions on further action to take, for a negative response; delivered to the in-field operator on the scanner itself via voice or text mobile communication, satellite phone, area wi-fi or radio, or to another location and operator via any suitable communication method including, as before, voice or text mobile communication, satellite phone, area wi-fi or radio, and, additionally, e-mail, land-line phone, and access to a private web page.

In a further embodiment, the data may also be collected and stored on the scanner for subsequent transmission when the scanner is in an area of better reception, based upon whatever transmission methodology is being used.

The manner and extent in which the data is forwarded to the relevant customer, or handled by the customer can be customised to the requests, needs and procedures of each customer and specific application.

Various alterations and modifications may be made to the present invention without departing from the scope of the invention.

What is claimed is:

1. A method of sequentially collecting a plurality of spectral responses for analysing mixtures of materials, the method comprising the steps of:
   sequentially illuminating a section of an object with one or more forms of stimulation, the mixture of materials associated with the object;
   sequentially measuring spectral emission and/or reflection and/or absorption obtained from the object resulting from the forms of stimulation, wherein sequentially measuring spectral emission and/or reflection and/or absorption obtained from the object resulting from the forms of stimulation can selected from a group consisting of: visible absorption, IR absorption, UV absorption, anti-stokes emissions, emissions with long wave UV stimulation, emissions with short wave UV stimulation, emissions with IR stimulation, emissions from phosphorescent materials, Raman spectroscopy or combinations thereof; and
   analyzing data from each measurement to identify whether the mixture of materials comprises a unique marker.

2. The method of claim 1, wherein illuminating indicates whether or not the mixture of materials is present.

3. The method as claimed in claim 1, wherein the mixtures of materials are provided on the object directly or as part of the object, or on the surface of the object, or on a label on the object, or on a label on the packaging containing the object.

4. The method as claimed in claim 1, wherein the material is selected from the group consisting of: organics, inorganics, polymeric, molecular dyes or pigment, doped pigments, pigments doped with rare earth elements, q-dots or other nanomaterials or combinations thereof.

5. The method as claimed in claim 4, wherein the material is micro- or nano-encapsulated or coated on the object, or delivered as paint or ink, in a film, incorporated in the bulk of the object, as additives in polymeric and plastic materials, including polyolefin, polyesters and polycellulose, as a lubricant or a wetting agent or otherwise present on the surface of the object and in the molecular-level surface roughness of the object; tied to the object by chemical bonds or by physical attraction forces or combinations thereof.

6. The method as claimed in claim 1, wherein the step of illuminating a section of the object with forms of stimulation is achieved using LED's or other light-emitting devices such as lasers, arc lamps, OLED's, incandescent sources.

7. A method of verifying the authenticity of an item, comprising the steps of:
   applying a unique marker to the item, the unique marker being assigned a corresponding digital code stored in a database;
   remotely scanning the item collecting sequentially several types of spectral responses using a single portable device by sequentially illuminating a section of the item with one or more forms of illumination and sequentially measuring spectral emission and/or reflection and/or absorption obtained, wherein sequentially measuring spectral emission and/or reflection and/or absorption obtained from the object resulting from the forms of illumination can selected from a group consisting of: visible absorption, IR absorption, UV absorption, anti-stokes emissions, emissions with long wave UV stimulation, emissions with short wave UV stimulation, emissions with IR stimulation, emissions from phosphorescent materials, Raman spectroscopy or combinations thereof;
   obtaining data from each measurement; and
   comparing the scanned data with the corresponding digital code to verify the authenticity of the item.

8. The method as claimed in claim 7, wherein the step of comparing the scanned data with the corresponding digital code to verify the authenticity of the item further comprises accessing the corresponding digital code stored on a local or remote database.

9. The method as claimed in claim 7, wherein the step of comparing the scanned data with the corresponding digital code to verify the authenticity of the item further comprises accessing a remote database from a remote position and receiving verification or otherwise via voice or text mobile communication, satellite phone, area wi-fi, radio, e-mail or access to a private web page.

10. The method as claimed in claim 7, wherein the step of remotely scanning the item using sequential analysis of spectral emission and/or absorption and/or reflection from different forms of illumination further comprises logging the time and location of the scanning and stored on a local or remote database.

11. The method as claimed in claim 7, wherein the data obtained from the step of comparing the scanned data with the corresponding digital code to verify the authenticity of the item are held locally for subsequent transmission.

12. An apparatus for analysing mixtures of materials used as a unique identifier, the mixtures of materials being applied to at least one object, the apparatus comprising:
   illuminating means for sequentially illuminating a section of the object with forms of illumination;
   detection means for sequentially measuring spectral emission and/or reflection and/or absorption obtained from the object resulting from the forms of illumination, wherein the detection means for sequentially measuring spectral emission and/or absorption and/or reflection obtained from the object resulting from the forms of illumination is responsive to any of the following: reflection, visible absorption, IR absorption, UV absorption, anti-stokes emissions, emissions with long wave UV stimulation, emissions with short wave UV stimulation, emissions with IR stimulation, emissions from phosphorescent materials, Raman spectroscopy or combinations thereof; and
   processing means for obtaining data from each measurement, the data indicating the presence or not of the mixtures of materials.

13. The apparatus as claimed in claim 12, wherein the mixtures of materials are provided on the object directly or as part of the object, or on the surface of the object, or on a label on the object, or on a label on the packaging containing the object.

14. The apparatus as claimed in claim 12, wherein the material is selected from the group consisting of: organics, inorganics, polymeric, molecular dyes or pigment, doped pigments, pigments doped with rare earth elements, q-dots or other nanomaterials or combinations thereof.

15. The apparatus as claimed in claim 14, wherein the material is micro- or nano-encapsulated or coated on the object, or delivered as paint or ink, in a film, incorporated in the bulk of the object, as additives in polymeric and plastic materials, including polyolefin, polyesters and polycellulose, as a lubricant or a wetting agent or otherwise present on the surface of the object and in the molecular-level surface roughness of the object; tied to the object by chemical bonds or by physical attraction forces or combinations thereof.

16. The apparatus as claimed in claim 12, wherein the illuminating means for illuminating a section of the object with forms of illumination is provided by at least one LED or other light-emitting devices such as lasers, arc lamps, OLED's, incandescent sources.

17. The apparatus as claimed in claim 12, wherein the detection means for sequentially measuring spectral emission and/or absorption and/or reflection obtained from the object resulting from the forms of illumination is at least one: one or bi-dimensional CCD, back-thinned CCD, CCD strip, one-dimensional diode array, single-point photomultiplier, silicon or InGaAs detector.

18. The apparatus as claimed in claim 17, wherein the detection means for sequentially measuring spectral emission and/or absorption and/or reflection obtained from the object resulting from the forms of stimulation includes light-dispersing elements for different types of spectra.

19. The apparatus as claimed in claim 12, wherein the detection means for sequentially measuring spectral emission and/or absorption and/or reflection obtained from the object resulting from the forms of illumination are multiple detectors sensitive in different spectral regions.

20. A hand-held apparatus for remotely analysing mixtures of materials used as a unique identifier, the mixtures of materials being firstly applied to at least one item, the apparatus comprising:
   illuminating means for sequentially illuminating a section of the item with forms of illumination;
   detection means for sequentially measuring spectral emission and/or reflection and/or absorption obtained from the item resulting from the forms of illumination, wherein the detection means for sequentially measuring spectral emission and/or absorption and/or reflection obtained from the object resulting from the forms of illumination is responsive to any of the following: reflection, visible absorption, IR absorption, UV absorption, anti-stokes emissions, emissions with long wave UV stimulation, emissions with short wave UV stimulation, emissions with IR stimulation, emissions from phosphorescent materials, Raman spectroscopy or combinations thereof; and
   processing means for obtaining data from each measurement, the data indicating the presence or not of the mixtures of materials.

* * * * *